United States Patent [19]
Higgins et al.

[11] Patent Number: 6,018,981
[45] Date of Patent: Feb. 1, 2000

[54] TEST KIT FOR MEASURING VAPOR EMISSION FROM A PLANAR SURFACE AND METHOD

[75] Inventors: Craig A. Higgins; Robert C. Higgins; Stanley S. Kuerbis, all of San Diego, Calif.

[73] Assignee: Sinak Corporation, San Diego, Calif.

[21] Appl. No.: 09/098,023

[22] Filed: Jun. 15, 1998

[51] Int. Cl.[7] ..................................................... G01N 1/22
[52] U.S. Cl. ............................. 73/19.01; 73/19.12; 73/73
[58] Field of Search ................................ 73/29.05, 31.07, 73/23.2, 864.51, 73, 19.01, 19.12; 422/61, 88

[56] References Cited

U.S. PATENT DOCUMENTS 2,534,279  12/1950  Liberthson .................................. 73/73

*Primary Examiner*—Michael Brock
*Attorney, Agent, or Firm*—Donald L. Beeson

[57] ABSTRACT

A test kit for measuring vapor emission from a concrete floor or other planar surface prior to installing a flooring material includes a relatively rigid dome-shaped cover having an outer bottom rim for seating with the planar surface to be tested when the cover is placed on the surface over an uncovered container of moisture absorptive material such as calcium chloride. The test kit further includes a weight ring that is removably placed onto a shoulder portion of the cover located at the cover's outer bottom rim. Placement of the weight ring on the dome-shaped cover during tests acts to hold the outer bottom rim of the cover in seating contact with the test surface. The test kit is easy to use and provides for reusable components. It can also be used without leaving a residue on the test surface.

24 Claims, 2 Drawing Sheets

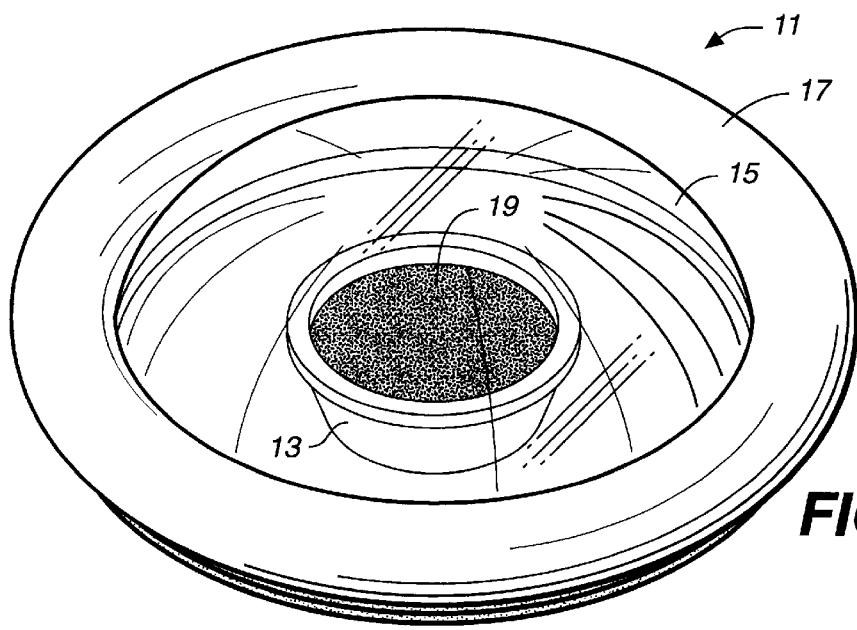
FIG._1
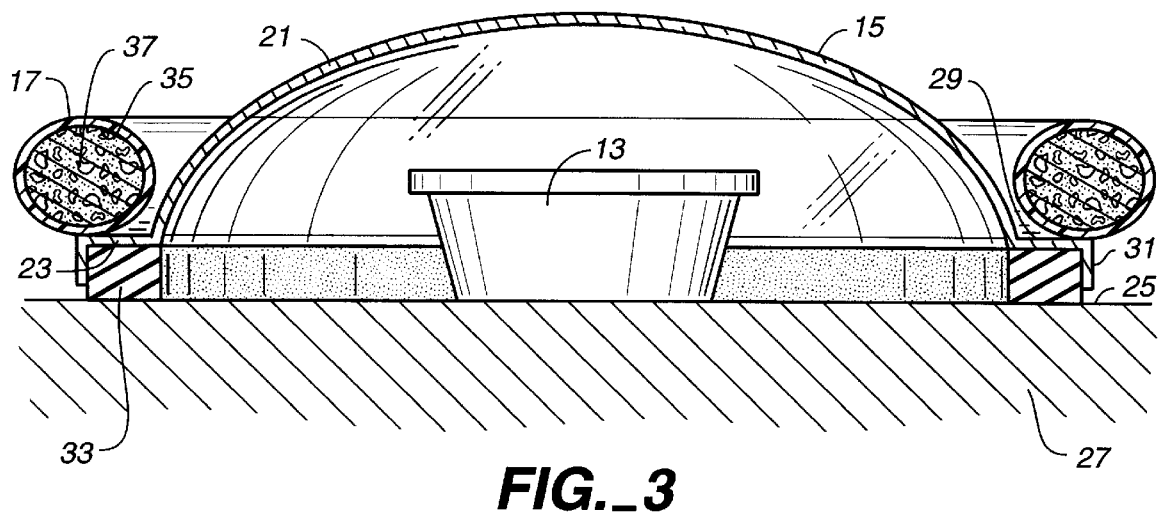
FIG._3

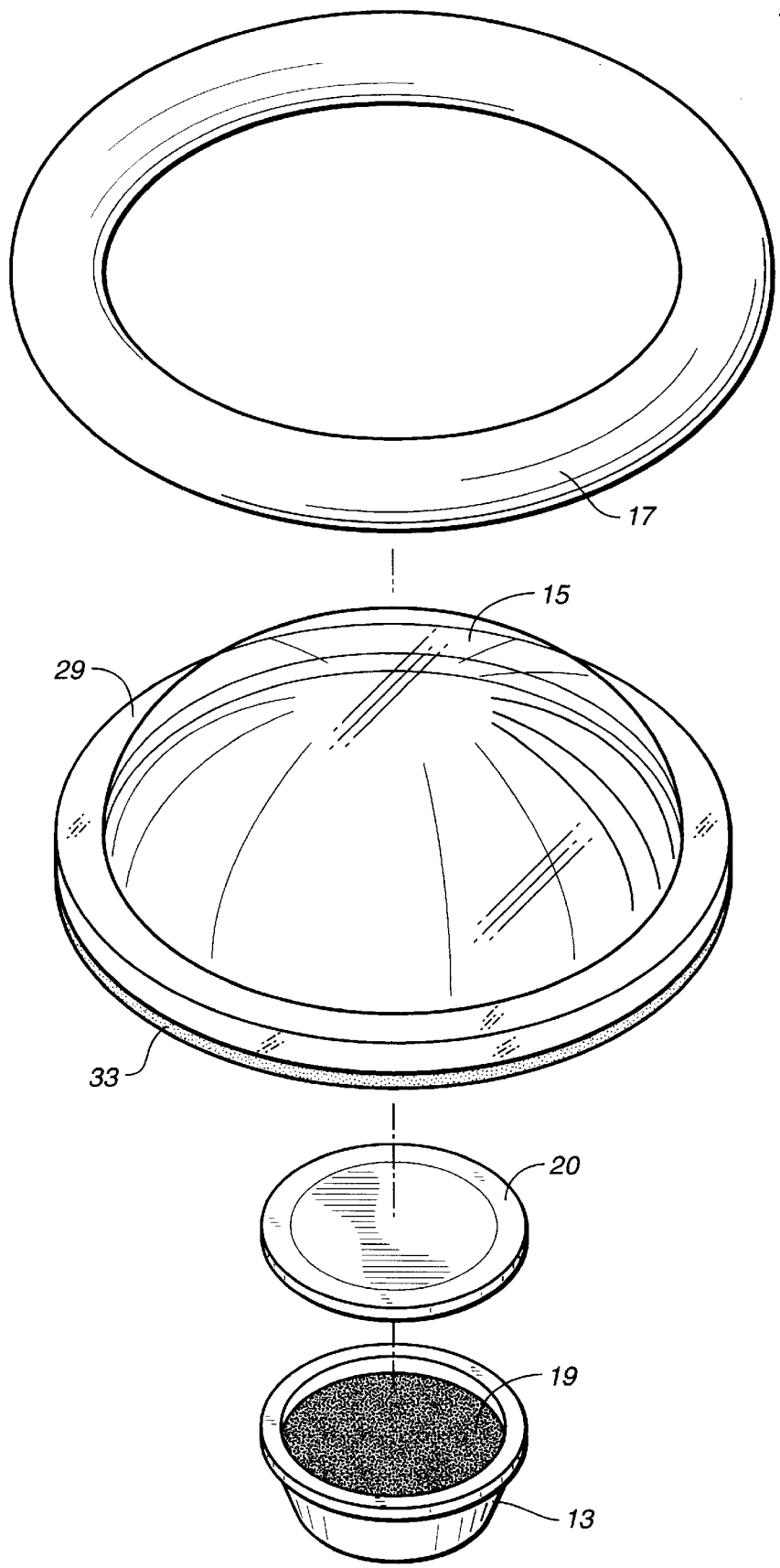
FIG._2

TEST KIT FOR MEASURING VAPOR EMISSION FROM A PLANAR SURFACE AND METHOD

BACKGROUND OF THE INVENTION

The present invention generally relates to techniques and devices for measuring vapor emission, and more particularly to test kits and methods for measuring vapor emission from a planar surface. The invention has particular application in quantifying vapor emission from concrete floors prior to installing a floor covering.

Floors that emit excessive moisture will detrimentally affect a floor covering installation. For this reason, floor manufacturers typically specify maximum allowable vapor emission for each specified flooring material offered by the manufacturer. For example, normal allowable vapor emission for sheet vinyl and hardwood floors is 3 pounds, where "pounds" indicates the measured weight of moisture emitted from 1,000 square feet of floor over a 24-hour period. The limit for vinyl composition tile (VCT) is typically 5 pounds. Some carpeting can withstand vapor emission levels up to about 7 pounds.

In the flooring industry, calcium chloride kits have become widely used for taking measurements of vapor emission from concrete floors prior to installing a floor covering. Such kits typically consist of a plastic "petri dish" containing about 30 grams of calcium chloride, a substance having good moisture absorption properties, and a larger cover which during a test is placed on the floor over the calcium chloride filled petri dish. Heretofore, the cover component of the test kit has been fabricated of a thin, clear plastic material that resembles a square or rectangular cake pan with a flange around the edge. Such prior test kit covers typically have a footprint of about 70 to 72 square inches and a height of about 1½ inches and are sealed to the floor using a putty-like sealing material, such as butyl, in order to maintain airtight contact with the floor. The difficulty with these kits is that they are cumbersome to install, requiring absolute cleaning of all particulate matter from the floor, and meticulous pressing around the edge to achieve an airtight seal around the entire cover perimeter. Also, after the test is completed the sealant must be peeled off the floor, which normally leaves a residue which must be removed. The pre-cleaning, the placement and retrieval of the cover, and post-test cleaning of residue from the floor's test surface can consume 20 minutes or more for each vapor emission test.

Another drawback of conventional calcium chloride test kit designs is that the test kit is not reusable, since the cover is destructibly removed after test. Thus, with conventional kit designs a new test kit is typically used for each measurement, with no opportunity for recycling.

The present invention overcomes the above-mentioned disadvantages of conventional calcium chloride test kits, by providing a test kit and method for measuring vapor emission from concrete floors and other planar surfaces using test kit components that are reusable. The invention further provides a vapor emission test kit that simplifies the placement and retrieval of the test kit from the test surface, eliminates the need to clean the test surface after use, and generally reduces the amount of time required to set up and conclude a test.

SUMMARY OF THE INVENTION

The invention involves a vapor emission test kit comprised of a relatively rigid cover for covering a vapor absorption material placed on a planar test surface, and a weighted mass that fits onto the cover for holding the cover in seating contact with this surface. Generally, the cover portion will have a base portion at which sealing contact between the planar surface and the cover is made. Preferably, the base portion is provided in the form of an outer bottom rim of a generally dome-shaped cover. Also preferably, a sealing element is provided around the cover's bottom rim to create a suitable sealing interface between the planar test surface and the cover.

The weighted mass of the test kit is preferably provided in the form of a weight ring sized to removably fit over and rest on the dome-shaped cover for holding the outer bottom rim of the cover in seating contact with the planar surface. However, it is understood that a weighted mass of other shapes might be used, such as a weighted blanket that can be replaceably laid over the cover. However, a ring-shaped weight is considered the best mode of the invention in that it is easily handled and can be sized to concentrate weight at the outer rim of the cover during test. Suitably, a radially extending shoulder portion is provided on the cover above the cover's bottom rim to provide a platform for receiving the weight ring.

In the preferred embodiment of the invention a sealing element is provided at the outer bottom rim of the cover to provide an airtight sealing interface between the test surface and the cover. In other words, seating contact of the cover with the test surface is achieved through the sealing element. However, the invention contemplates the possibility that the cover will seat directly on the test surface without the need for a separate sealing element. In such a case, the integrity of the test may be compromised somewhat if the seating contact is not sufficiently airtight.

The invention also involves a method for measuring vapor emission from a planar surface such as a concrete floor. The method includes the steps of placing a vapor absorption material in a dish-like container, weighing the container, preparing a planar surface to be measured, and placing the weighed container on the prepared surface. A rigid cover having an outer bottom rim which seats on the planar test surface is then placed over the container of vapor absorption material such that the cover surrounds the container. A weight ring is then placed over the cover in order to firmly hold it in seating contact with the surface during a defined test period. At the conclusion of the test period, the weight ring and cover are easily and non-destructively removed, and the container re-weighed to determine the amount by weight of moisture absorbed during test.

Therefore, it can be seen that a primary object of the present invention is to provide an improved test kit and method for measuring vapor emission from a concrete floor or other planar surface prior to installing a floor covering. It is another object of the invention to provide a vapor emission test kit that is easy to use, that reduces placement and retrieval time, and that has reusable components. It is a further object of the invention to provide a vapor emission test kit that reduces waste and which eliminates the need for cleaning post-test residue from the tested surface. Further objects of the invention will be apparent from the following specifications and claims, as well as from the accompanying drawings.

DESCRIPTION OF THE DRAWINGS

FIG. 1 is a top perspective view of a test kit in accordance with the invention.

FIG. 2 is an exploded top perspective view of the test kit shown in FIG. 1, with the addition of a lid for the container for the moisture absorption medium.

FIG. 3 is a cross-sectional view, in side elevation, of the test kit shown in FIG. 1.

DETAILED DESCRIPTION OF THE ILLUSTRATED EMBODIMENT

Referring now to the drawings, a vapor emission test kit 11 is seen to include a dish-like container 13, a relatively rigid cover 15, and a weight ring 17. The container 13 is suitably sized to hold approximately 30 grams of calcium chloride, denoted by the numeral 19, which provides a moisture absorption medium for the vapor emission test hereinafter described. As shown in FIG. 2, the container 13 is provided with a suitable snap-lock lid 20 for sealing the container before and after test, so as to prevent moisture absorption by the calcium chloride other than during the test period.

The cover 15 of the test kit, which is fabricated of a suitably thick and preferably clear plastic material, has a dome-shaped top 21 and a base portion in the form of an outer bottom rim 23. Outer rim 23, which rests on the planar surface 25 of concrete floor 27, includes a radially extending, annular shoulder 29 and a downward projecting outer lip portion 31. Preferably, the cover is sized to cover approximately one-half square foot of the tested surface 25, and therefore will preferably have a diameter of approximately 9½ inches.

The illustrated test kit also has a separate annular sealing element 33 suitably sized to fit beneath the cover's outer bottom rim 23 inside the rim's projecting lip 31. This sealing element acts to provide an airtight seal between the cover's bottom rim 23 and the planar test surface 25 when the cover is placed on the test surface under the weight of weight ring 17. The sealing element can be provided using commercially available seals or gaskets, such as a refrigerator door-type gasket, and can, if desired, be adhered to the underside of the cover's bottom rim by a suitable adhesive. If and when the sealing element wears out or deteriorates from age, it can be easily replaced.

Weight ring 17 provides a weighted mass that can be placed on the cover of the test kit to hold the cover in seating contact with the planar surface 25 and to maintain an airtight seal around the cover's outer bottom rim 23 during test. The weight ring is suitably fabricated from a length of plastic hose 35 filled with a high density, heavy aggregate material 37, such as steel shot. Preferably, the ring is sized to fit entirely over the cover so that it rests on top of the shoulder portion 29 at the cover's outer bottom rim. Such sizing will ensure that the weight of the ring is evenly distributed around the perimeter of the cover and directly over the sealing element 33 which provides the sealing interface with planar test surface 25. However, it is understood that the ring could have a smaller diameter than shown in the accompanying drawings so that it rests further up on the dome-shaped top 21 of the cover. It will also be appreciated that the weight ring could be provided in a more flexible form, such as a suitably heavy chain that could be drape around the cover. However, the formed weight ring described herein is more easily handled.

The use of the illustrated test kit of the invention to measure the vapor emission from a concrete floor will now be described in connection with describing the method of the invention.

As a first step to utilizing the test kit, the surface to be tested, planar surface 25 in the drawings, must be prepared by mechanically removing all grease, oils, wax, curing compounds, and/or other coatings that may be present on the surface. Depending on the nature and condition of the floor, suitable methods of preparing the surface will include scraping, wire brushing or grinding the surface. Thereafter, the surface should be cleaned such as by sweeping, vacuuming, or blowing to remove all dust and debris.

Once the surface has been properly prepared, the container 13, which has been filled with a quantity of calcium chloride 19 and sealed closed with lid 20, is weighed and its weight recorded. Lid 20 is then removed from the container and the container placed on the prepared surface of the floor, whereupon the dome-shaped cover 15 is placed over the container. The dome-shaped cover should have suitable resiliency such that it can be pushed down to "burp" the cover, that is, to expel a quantity of air from underneath the cover in order to draw a partial vacuum which will assist in holding the cover to the floor.

Once the cover is in place and has been "burped," the weight ring 17 is placed over the shoulder 23 of the cover's outer perimeter rim 29 to hold the cover in place during the test period. With the cover held down by the weight ring, the kit should remain in place, undisturbed, on the prepared surface for a pre-set period of time, typically 60–72 hours. At the conclusion of the test period, the weight ring and cover are simply lifted from the test surface 25, with no destructive effect to the cover, and container 13 retrieved and again sealed by lid 20 so as to prevent spillage and further moisture absorption by the calcium chloride. The container is then re-weighed. The difference in the recorded weights of the calcium chloride filled container can then be computed and the absorption converted to a standardized measure of vapor emission in "pounds" using well known conversion formulas.

Since the components of the test kit are neither damaged nor destroyed during the test procedure, they can be reused for subsequent testing procedures. Thus, there will be no need to discard any portion of the test kit after the test is complete, other than the calcium chloride absorption medium.

Thus, it can be seen that the present invention provides a greatly improved test kit and method for measuring vapor emission from a planar surface. The invention also provides a test kit which is easy to use, inexpensively fabricated, and fully reusable. While the invention has been described in considerable detail in the foregoing specification and in the accompanying drawings, it will be understood that it is not intended that the invention be limited to such detail except as necessitated by the following claims. For example, it will be understood that the cover portion of the test kit and the kit's weight ring could be made in shapes other than those illustrated in the drawing, such as a square shape, or that the elements of the test kit can be made of suitable materials other than indicated in the specification. Moreover, the base portion of the cover which seats on the test surface could be provided other than at the outer rim of the cover, such as providing an interior cylinder base over which the top portion of the cover extends for holding the weight ring. Still further a cover could be provided without a shoulder portion such that the outer bottom rim of the cover consists simply of a narrow edge. In such an embodiment a suitable airtight sealing interface should be provided between the edge of the cover and the planar surface. Yet another alternative of the invention might be to affix the weight ring or other weighted mass permanently to the test kit cover such that the weight ring is not a separate part.

We claim:

1. A test kit for measuring vapor emission from a planar surface, said test kit comprising a substantially rigid cover for covering a vapor absorption material on a planar surface, said cover having a base portion for seating with the planar surface when the cover is placed on said surface, and at least one weighted mass fitted on to said cover for holding the cover in seating contact with the planar surface around the base portion thereof.

2. The test kit of claim 1 wherein said weighted mass is a separate and removable component.

3. The test kit of claim 1 wherein said cover is dome-shaped and has a base portion in the form of an outer bottom rim.

4. The test kit of claim 3 wherein said weighted mass is provided in the form of a weight ring sized to re movably fit over and rest on said dome-shaped cover for holding the outer bottom rim of the cover in seating contact with the planar surface.

5. A test kit for measuring vapor emission from a planar surface, said test kit comprising a substantially rigid cover for covering a vapor absorption material on a planar surface, said cover having an outer bottom rim for seating with the planar surface when the cover is placed on said surface, a shoulder portion on said cover at the outer bottom rim thereof, and a weight ring sized and shaped to removably fit over said cover and rest on the top shoulder portion of said cover for holding the outer bottom rim of said cover in seating contact with the planar surface.

6. The test kit of claim 5 wherein said cover is fabricated of a resilient material such that the cover can be resiliently depressed on a planar surface to draw a partial vacuum under the cover.

7. The test kit of claim 5 wherein said cover material is clear plastic.

8. The test kit of claim 5 wherein said cover has a dome-shape.

9. The test kit of claim 5 wherein said weight ring is a flexible hose filed with heavy high density aggregate material.

10. The test kit of claim 5 wherein a sealing element is provided at the outer bottom rim of the cover for providing a non-adhesive sealing interface between said outer bottom rim and the planar surface to be tested.

11. The test kit of claim 10 wherein said sealing element is affixed to the outer bottom rim of said cover.

12. A test kit for measuring vapor emission from a planar surface, said test kit comprising a substantially rigid dome-shaped cover for covering a vapor absorption material on a planar surface, said cover having an outer bottom rim for seating with the planar surface to be tested when the cover is placed on said surface, an annular shoulder portion on said cover at outer bottom rim thereof, a separate non-adhesive sealing element at the outer bottom rim of the cover for providing a sealing interface between said outer bottom rim and the planar surface to be tested, and an annular weight ring sized to removably fit over said cover and rest on the annular shoulder portion thereof for holding the outer bottom rim of said cover and said sealing element in seating contact with the planar surface.

13. The test kit of claim 12 wherein said cover is fabricated of a rigid but resilient material that can be resiliently depressed on a planar surface to draw a partial vacuum under the cover.

14. The test kit of claim 12 wherein said weight ring is a flexible hose filed with heavy high density aggregate material.

15. The test kit of claim 12 wherein an annular sealing element is affixed to the outer bottom rim of said cover.

16. A test kit for measuring vapor emission from a planar surface, said test kit comprising a dish-like container for holding a vapor absorption material on the planar surface, a substantially rigid dome-shaped cover for covering said container, said cover having an outer bottom rim for seating with the planar surface when the cover is placed on said surface, an annular shoulder portion on said cover above outer bottom rim thereof, and an annular weight ring sized to removably fit over said cover and to rest on the annual shoulder portion thereof for holding the outer bottom rim of said cover in seating contact with the planar surface.

17. The test kit of claim 16 wherein a separate non-adhesive sealing element is provided at the outer bottom rim of the cover for providing a sealing interface between said outer bottom rim and the planar surface to be tested.

18. The test kit of claim 16 wherein said container is provided with a snap-lock lid for sealing the container closed before and after a test.

19. A method of measuring vapor emission from a planar surface, said method comprising weighing a container filled with a vapor absorption material which is sealed closed, preparing a planar surface to be measured, opening the weighted container to expose the vapor absorption material therein and placing the container on the prepared planar surface, placing a substantially rigid dome-shaped cover on said prepared planar surface over said open container wherein said cover has an outer bottom rim for seating with the planar surface when the cover is placed on said surface, removably placing a weighted mass over said cover such that the outer bottom rim of said cover is held firmly in seating contact with the planar surface, leaving the cover and weighted mass in place for a defined test period, removing the weighted mass and then the cover from the planar surface, sealedly closing the container to prevent further moisture absorption by the vapor absorption material therein, and re-weighing the closed container holding the vapor absorption material to determine the amount by weight of moisture absorption during the defined test period.

20. The method of claim 19 wherein said cover is fabricated of a resilient material and said method further comprises the step of resiliently depressing the cover on the planar surface to draw a partial vacuum thereunder when measuring vapor emission from the planar surface.

21. The method of claim 20 wherein said cover is resiliently depressed after the weighted mass is placed on said cover.

22. The method of claim 19 wherein, before placing the cover over the open container, a separate sealing element is fitted around the outer bottom rim of the cover for providing a sealing interface between said outer bottom rim and the planar surface to be tested.

23. The method of claim 19 wherein said dome-shaped cover has a shoulder portion above the cover's outer bottom rim and said weighted mass is in the form of a weight ring sized to rest on said shoulder portion when said weight ring is removably placed over said cover.

24. The method of claim 19 wherein the same cover and weight ring are reused for repeated measurements.

* * * * *